United States Patent
Cole et al.

(10) Patent No.: US 6,429,018 B1
(45) Date of Patent: Aug. 6, 2002

(54) PRENATAL SCREENING FOR DOWN'S SYNDROME USING HYPERGLYCOSYLATED GONADOTROPIN

(75) Inventors: Laurence A. Cole, Albuquerque, NM (US); Andrew Kardana, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 09/254,377

(22) PCT Filed: Sep. 5, 1997

(86) PCT No.: PCT/US97/16657

§ 371 (c)(1),
(2), (4) Date: Nov. 29, 1999

(87) PCT Pub. No.: WO98/10282

PCT Pub. Date: Mar. 12, 1998

Related U.S. Application Data

(60) Provisional application No. 60/025,568, filed on Sep. 6, 1996.

(51) Int. Cl.[7] .................. G01N 33/49; G01N 33/493; G01N 33/531; G01N 33/00; C07K 16/26

(52) U.S. Cl. .................. 436/87; 436/86; 436/501; 436/510; 436/518; 436/817; 436/570; 436/536; 436/547; 436/548; 436/808; 436/813; 436/814; 436/818; 437/7.1; 437/7.21; 437/7.9; 437/7.92; 437/7.93; 437/7.94; 437/7.95; 437/806; 424/1.1; 424/100

(58) Field of Search .................. 436/63–65, 87, 436/86, 813, 814, 818, 510–511, 518, 501, 570, 547–548, 906, 811, 817, 536, 808; 424/1.1, 100; 435/212, 219, 7.1, 7.93, 7.21, 7.92, 7.94, 7.95, 806, 7.9

(56) References Cited

U.S. PATENT DOCUMENTS

| | | |
|---|---|---|
| 4,874,693 A | 10/1989 | Bogart |
| 5,252,489 A | 10/1993 | Macri |

(List continued on next page.)

FOREIGN PATENT DOCUMENTS

| | | |
|---|---|---|
| EP | 698 793 A2 | 2/1996 |

OTHER PUBLICATIONS

Spencer., "Evaluation of an assay of the free beta subunit of choriogonadotropin and its potential value in screening for Down's syndrome.", Clinical Chemistry, vol.37, No. 6, pp. 809–814, 1991.*

(List continued on next page.)

*Primary Examiner*—Long V. Le
*Assistant Examiner*—Lisa V. Daniels-Cook
(74) *Attorney, Agent, or Firm*—Mary M. Krinsky

(57) ABSTRACT

A prenatal screening method for Down's syndrome involves assaying for hyperglycosylated gonadotropin in biological test samples such as urine, plasma or serum obtained from pregnant women. Hyperglycosylated gonadotropin comprises a variant population of chorionic gonadotropin, chorionic gonadotropin-free β-subunit, β-core fragment, and/or free α-subunit exhibiting differences in the carbohydrate content from what is observed in samples obtained from pregnant women carrying normal fetuses. Qualitative or quantitative observation of differences in the carbohydrate content of the hyperglycosylated gonadotropin population from corresponding control samples containing a normal gonadotropin population, or direct observation of the variant species seen in Down's syndrome, indicates that the woman's fetus has Down's syndrome. Typical screens involve carbohydrate analyses, immunoassays, or combinations of these methods. Some embodiments employ a lectin such as concanavalin A reactive to the carbohydrate moiety; others employ antibodies to at least one hyperglycosylated gonadotropin species.

20 Claims, 6 Drawing Sheets

U.S. PATENT DOCUMENTS 5,356,817 A * 10/1994 Cole .......................... 436/64
5,445,968 A *  8/1995 Blithe et al. ................. 436/510
5,506,150 A *  4/1996 Canick et al. .............. 436/510
5,674,727 A * 10/1997 Cole et al. .................. 435/219

OTHER PUBLICATIONS

Birken, S., et al., Endocrinology 123:572–583 (1988).
Blithe, D.L., et al., Endocrinology 122:173–180 (1988).
Bogart, M.H., et al., Prenatal Diagnosis 7:623–630 (1987).
Cole, L.A., et al., Prenatal Diagnosis 17:607–614 (1997).

Howanitz, J.H., Arch. Pathol. Lab. Med. 117:369–372 (1993).

Jauniaux, E., et al., J. Endocrinology 148:27–31 (1996).

Kardana, A., et al., Endocrinology 129:1541–1550 (1991).

Masure, H.R., et al., J. Clin. Endocrinology & Metabolism 53:1014–1020 (1981).

O'Connor, J.F., et al., Third World Conference on Early Pregnancy Abstract 66 (Oct. 3–6, 1996).

* cited by examiner

PRENATAL SCREENING FOR DOWN'S SYNDROME USING HYPERGLYCOSYLATED GONADOTROPIN

RELATED APPLICATION DATA

This application claims priority benefit of U.S. patent application Ser. No. 60/025,568, filed Sep. 6, 1996, and PCT application number PCT/US97/16657, filed internationally Sep. 5, 1997.

TECHNICAL FIELD

This invention relates to a Down's syndrome screening test for pregnant women.

A triple screen of α-fetoprotein, chorionic gonadotropin and unconjugated estrogen in serum has been suggested for the prenatal diagnosis of Down's syndrome (Bennett, J. C., and Plum, F., *Cecil's Textbook of Medicine*, W. B. Saunders, Philadelphia, 1996, p. 165). However, it allows detection of only 60 to 65% of fetuses with the genetic disorder and gives 5% false positive results. It is also limited to the second trimester of pregnancy (15 to 24 weeks of gestation), and has become expensive as significant license fees are being levied on laboratories running human chorionic gonadotropin analyses using conventional methods (Auxter, S., *Clin. Labor News* 23: 1–3 (1997)).

Definitive prenatal diagnosis of fetal chromosome abnormalities leading to Down's syndrome, which affect 1 in 700 live births, typically involves instead culture of amniocytes at midtrimester gestation. The procedure involves the aspiration of a small sample of amniotic fluid (amniocentesis), culturing of the fetal cells contained in the fluid, and determination of the karyotype of these cells and thus the fetus. The major indications for the use of this technique for the detection of chromosome abnormalities are maternal age (usually offered to all mothers over the age of 35 at the time of expected delivery), the presence of a parental chromosome abnormality, or a maternal history of carrying a previous trisomic child or aborted fetus karyotyped to be trisomic. Direct transcervical aspiration of chorionic villi (chorionic villus sampling, or CVS) has also been used for prenatal diagnosis.

Though both procedures have been shown to be relatively safe and reliable, it is generally accepted that they involve some risk, including risk of miscarriage, and, in the case of CVS, also risk of limb hypoplasia in babies born following the procedure. It would be desirable to have other methods for screening pregnant women for Down's syndrome fetuses, particularly screens that are noninvasive and sensitive. Most Down's syndrome cases occur in younger pregnant women, those under 35 at the time of expected delivery, or the majority of pregnancies. Less invasive screening tests are needed employing serum or urine samples to identify those at high risk for Down's syndrome pregnancies, who may not want the risk of amniocentesis or CVS.

BACKGROUND OF THE INVENTION

Human chorionic gonadotropin (hCG) is a glycoprotein hormone secreted in relatively large quantities by the trophoblast cells of the placenta (Masure, H. R., et al., *J. Clin. Endocrinol. Metab.* 53: 1014–1020 (1981)). hCG is composed of two dissimilar subunits, α (92 amino acids and two N-linked oligosaccharides) and β (145 amino acids and two N-linked and four O-linked oligosaccharides), joined noncovalently, and is detected in the serum and urine of pregnant women and in those with trophoblast disease (hydatidiform mole and choriocarcimoma). Free α- and free β-subunits, and degraded hCG and free β-subunit molecules are also detected in serum and urine samples (Birken, S., et al., *Endocrinology* 122: 572–583 (1988)). The degraded molecules include nicked hCG and nicked free β-subunit, each cleaved between β-subunit residues 47 and 48 (or less commonly between residues 43 and 44 or 44 and 45), nicked β-subunit missing all or part of the C-terminal sequence (β93–145) and, a terminal degradation product comprising two fragments, β-subunit sequences 6–40 and 55–92, held together by disulfide linkages, found primarily in urine samples (FIG. 1). The terminal degradation product has no O-linked oligosaccharides and degraded N-linked oligosaccharide moieties, one or two N-linked pentasaccharides, versus two undecasaccharides on free β-subunit and hCG (FIG. 2A). The terminal degradation product was called β-core fragment (β-core, Blithe, D., et al., *Endocrinology* 122: 173–180 (1988)), firstly because of its small size (~9,000 daltons; hCG is 37,000 daltons), and secondly because of its retention of hCGB radioimmunoassay or β-submit core antisera (versus C-terminal or other) immunoreactivity (Birken, et al., and Masure, et al., cited above). Through most of a pregnancy, β-core fragment is the principal hCG β-subunit-related molecule in urine samples.

Serum and urine free β-subunit derive from three sources: direct section by trophoblast cells, slow dissociation of circulating hCG into free α- and β-subunits, and by the nicking of hCG by macrophage or neutrophil enzymes associated with trophoblast tissue, and the more rapid dissociation of nicked hCG in circulation (FIG. 1). Free β-subunit may be nicked by nicking enzymes in the circulation. Urine β-core fragment appears to derive from the degradation of nicked free β-subunit in the kidney.

In the late 1980s, the triple marker test mentioned above was developed to screen for Down syndrome pregnancies. It combined maternal age with serum measurements of hCG, α-fetoprotein, and unconjugated estriol (Bogart, M. H., et al., *Prenat. Diagn.* 7:623–630 (1987), U.S. Pat. No. 4,874, 693 to Bogart, Wald, N. J., et al., *Br. J. Obstet. Gynaecol.* 95: 334–341 (1988), and Canick, J. A., *J. Clin. Immunoassay* 13: 30–33 (1990)). More recently, serum-free β-subunit tests and free β-subunit-α-fetoprotein combinations have been introduced as alternative Down syndrome-screening methods (Macri, J. N., el al., *Am. J. Obstet. Gynecol.* 163: 1248–1253 (1990) and Spencer, K., et al., *Ann. Clin. Biochem.* 30: 394–401 (1993)). The best serum free β-subunit combination, or the optimal triple marker test, however, detects only 60 to 65 percent of Down's syndrome cases, with a 5 percent false-positive rate. At these detection and false-positive rates, approximately 80 amniocenteses need to be performed to detect a single case of Down syndrome, and a significant number of Down's syndrome cases are missed (Cole, L. A., et al., *Prenatal Diagnosis* 17: 607–614 (1997)). There is a need for improvement in prenatal screening methods.

SUMMARY OF THE INVENTION

It is an object of the invention to provide a prenatal screening test for Down's syndrome pregnancies.

It is another and more specific object of the invention to provide a sensitive, noninvasive test for Down's syndrome fetuses in pregnant women.

It is a further object of the invention to provide an improvement in the triple marker test that exhibits a decreased false positive rate.

These and other objects are accomplished by the present invention, which provides a novel diagnostic method for screening for the presence or absence of Down's syndrome in the fetus of a pregnant woman which comprises obtaining a biological test sample from the woman and determining the presence of Down's syndrome by observation of hyperglycosylated gonadotropin in the sample. This typically involves measuring the concentration of hyperglycosylated gonadotropin, its free β-subunit, its free α-subunit, and/or its β-core fragment in the test sample, and determining the presence of Down's syndrome by observation that the concentration in the test sample population differs from a normal hyperglycosylated gonadotropin or free α-subunit, free β-subunit, or β-core fragment population and/or is the same as, or similar to, a Down's syndrome population. In preferred embodiments, the test sample is urine, saliva, plasma or serum, the population comprises hyperglycosylated hCG, β-core fragment, free α-subunit, free β-subunit, and mixtures thereof, and any differences between the properties observed in the normal and Down's syndrome samples reflect differences observed in the carbohydrate content of the glycopolypeptides and/or glycopeptides.

Carbohydrate compositional or structural analyses, immunoassays, and combinations of these methods are generally employed. In some embodiments, hyperglycosylated gonadotropin is determined directly by assay for at least one hyperglycosylated species, i.e., variant hCG, free β-subunit, free α-subunit, and/or β-core fragment. These screens typically employ a monoclonal, polyclonal, or fusion phage antibody to a hyperglycosylated or carbohydrate-variant hCG species in an ELISA, Western blot, or the like. In another embodiment, elevated levels of monosaccharides are observed in samples positive for Down's syndrome. Other screens employ lectins that bind the carbohydrate moieties, chromatography, chemical or electrophoresis or isolectric focussing tests that detect glycosylation variants of hCG. Lectins may also be employed to separate and/or concentrate hCG species having aberrant carbohydrate moieties prior to immunoassay.

DESCRIPTION OF THE FIGURES

FIG. 3 illustrates hyperglycosylated N-linked and O-linked oligosaccharides on abnormal hCG species found elevated in Down's syndrome and/or related pathological conditions such as choriocarcinoma.

DETAILED DESCRIPTION OF THE INVENTION

This invention is based upon the observation of aberrant carbohydrate profiles in hCG species (hyperglycosylated gonadotropin) obtained from the serum or urine of pregnant women carrying Down's syndrome fetuses, but not from women carrying normal fetuses.

In the practice of the invention, the presence or absence of Down's syndrome in the fetus of a pregnant woman is determined by a method comprising obtaining a biological test sample from the woman and assaying for hyperglycosylated gonadotropin in the sample. This typically involves a determination of whether the composition or physical properties of the chorionic gonadotropin population in the test sample differs from a corresponding control sample containing a normal chorionic gonadotropin population and/ or that the sample contains elevated levels of at least one species of the hyperglycosylated gonadotropin population observed in Down's syndrome.

Figure 2A:
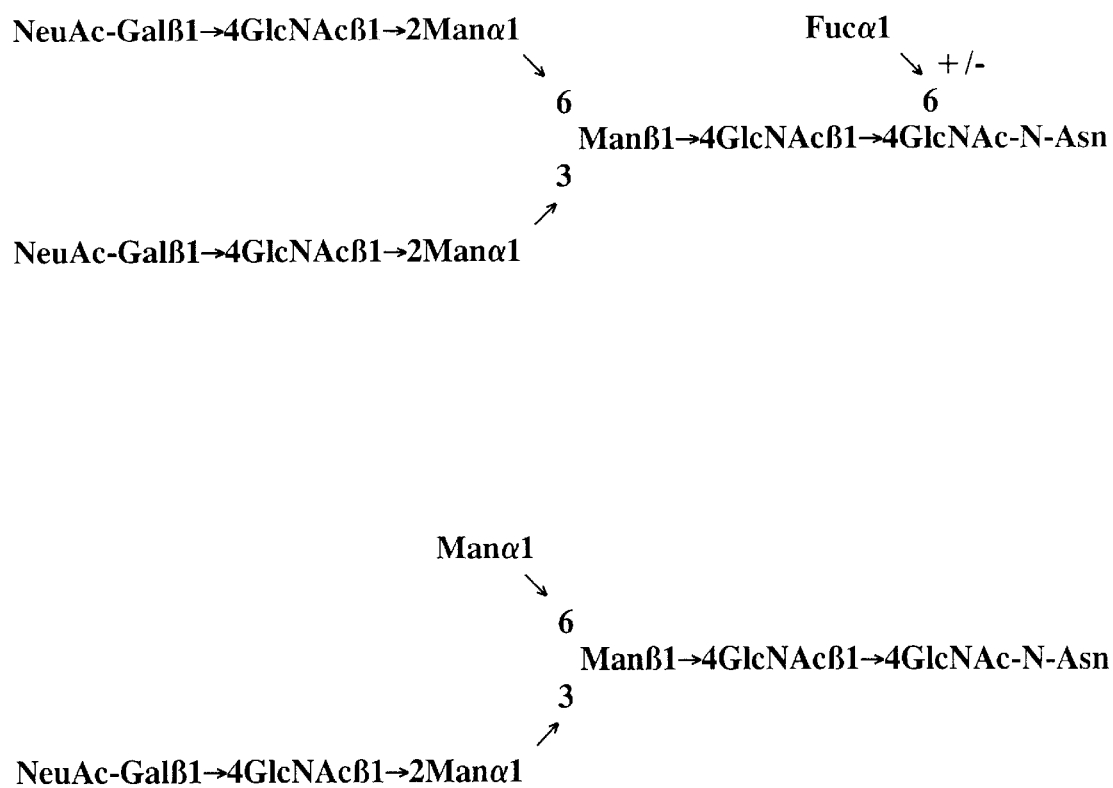
FIG. 2 shows schematic drawings of N-linked oligosaccharides. The structures in FIG. 2A illustrate the N-linked oligosaccharides on normal pregnancy hCG and its free β-subunit, and free α-subunit. The FIG. 2B structure shows a degraded N-linked oligosaccharide on a normal pregnancy β-core fragment. The FIG. 2C structure indicates the O-linked oligosaccharides on normal pregnancy hCG as its free β-subunit. Abbreviations used are Man for mannose, Gal for galactose, GlcNAc for N-acetylglucosamine, Fuc for fucose, and GalNAc for N-acetylgalactosamine. Variables are indicated by the ±.
Figure 2B:
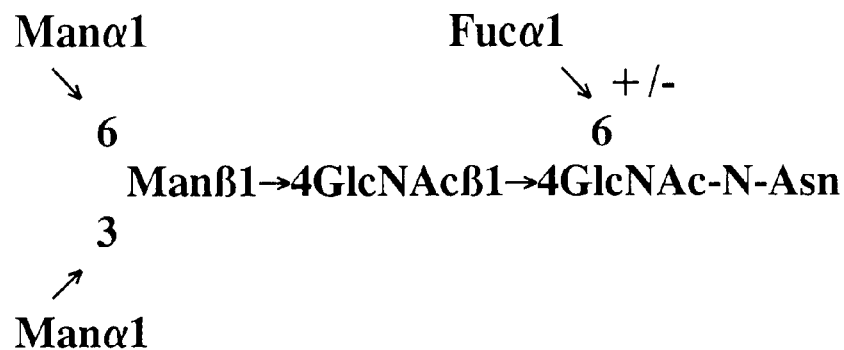
Figure 2C:
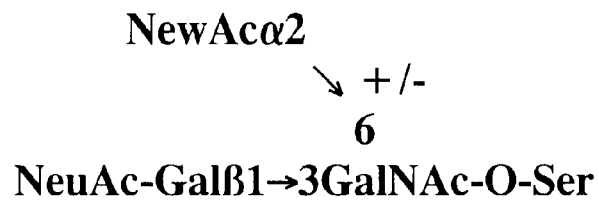
Figure 3A:
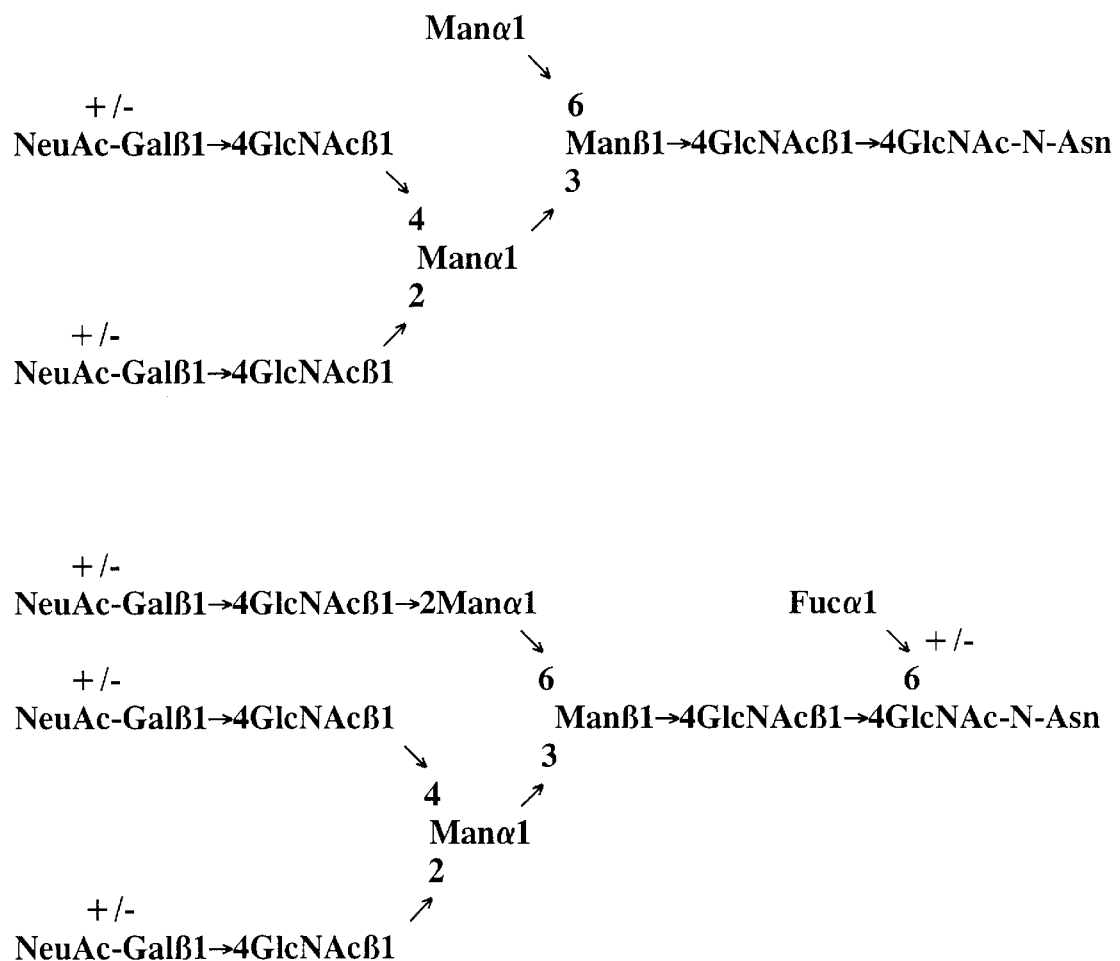
FIG. 3A shows N-linked oligosaccharides on hyperglycosylated gonadotropin and its free β-subunit and free α-subunit.
Figure 3B:
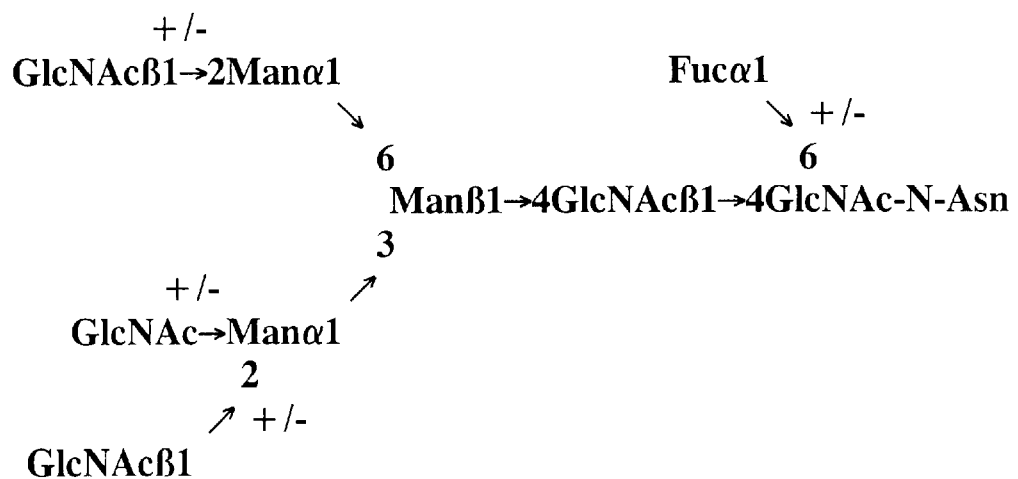
FIG. 3B shows N-linked oligosacchrides on hyperglycosylated gonadotropin β-core fragment.
Figure 3C:
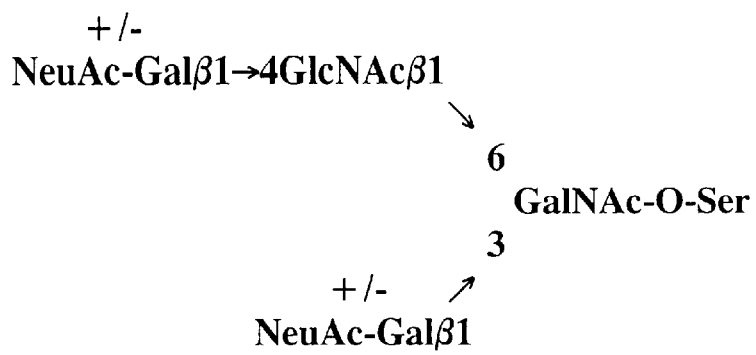
FIG. 3C shows O-linked oligosacchrides on hyperglycosylated gonadotropin and its free β-subunit. Abbreviations are the same as that employed in FIG. 2.

As used herein the term "chorionic gonadotropin population" includes chorionic gonadotropin, α-subunits, β-subunits, β-core fragments, and mixtures thereof, and specifically includes variants of these species that have abnormal monosaccharide compositions in their oligosaccharide moieties or are hyperglycosylated such as those observed in Down's syndrome hCG populations. The term "hyperglycosylated gonadotropin" generically encompasses these latter species within the chorionic gonadotropin population, comprising hyerglycosylated gonadotropin, nicked gonadotropin, α-subunits, β-subunits, β-core fragments, and mixtures of any of these which exhibit aberrant carbohydrate profiles and/or aberrant carbohydrate levels as compared to normal levels.

hCG and β-core fragments are employed in many embodiments. It is an advantage of the invention that pregnancy serum contains large quantities of hCG. hCG accounts for over 99% of the total β-immunoreactivity in pregnancy serum. Likewise, pregnancy urine has a large population of β-core fragment. Indeed, the β-core population can account for as much as 70% of the total β-immunoreactivity in pregnancy urine (Blithe, et al., cited above). Thus, in preferred embodiments, the invention provides a screening method for the abundant species, hCG in serum and β-core fragment in urine, and ones that are readily detected using standard techniques including immunoassays and the like clinical measurements described by Birkin, et al., and Blithe, et al., cited above and illustrated hereafter, or, because of variations observed in the carbohydrate portion of Down's syndrome hCG species, carbohydrate analyses such as use of a lectin specific to the carbohydrate, or use of monosaccharide compositions tests, electrophoresis or isoelectric focussing to detect glycosylation variants. Some variant species observed in Down syndrome and related aberrant pregnancies are illustrated in FIG. 3 and described in Elliott, M. M., et al., *Endocrine J.*, vol. 7 (1997). Note that many hyperglycosylated Down syndrome hCG species have, instead of a sialyllactosamine (NeuAc-Gal-GlcNAc) biantennary structure attached to a mannose core in the hCG β-subunit (FIG. 2), triantennary structures having an additional sialyllactosamine (FIG. 3A). Other hyperglycosylation features include increased levels of fucose-containing (versus fucose-free) N-linked oligosaccharides, and hexasaccharide structures at the β-subunit O-linked carbohydrate sites (FIG. 3C). Hyperglycosylation is thus significantly elevated in Down syndrome hCG species.

Any biological sample can be employed in methods of the invention, including, but not limited to, urine, saliva, serum, plasma, tears, and amnionic fluid. Saliva, urine, plasma or serum are preferred because samples are more voluminous and sampling involves no risk of harm to the fetus. Urine obtained from a pregnant woman in her first (generally defined as about 9 weeks to 13 weeks, 6 days) or second trimester (generally defined as about 14 to 28 weeks) and is particularly preferred in some embodiments. It is an advantage of the invention that samples can be analyzed in the first trimester, earlier in the pregnancy than previously described methods for assessing placental dysfunction such as that disclosed in U.S. Pat. No. 4,874,693 cited above (18 to 25 weeks). A screening method suitable for use from the 11th to the 19th weeks of gestation, for example, is illustrated in the Examples that follow and in FIG. 4.

Down's syndrome screens of the invention generally employ carbohydrate analyses, immunoassays, or combination of these methods for detection of hyperglycosylated gonadotropin, but any assay that functions to qualitatively or quantitatively determine variations in sample concentrations of hyperglycosylated gonadotropin from normal levels, and/ or detects abnormal carbohydrate hCG moieties in the sample's gonadotropin population can be employed in the practice of the invention. Direct assay for at least one member of the variant Down's syndrome chorionic gonadotropin population is preferred. Some screens employ lectins that assay for the carbohydrate moieties, chromatography, chemical or electrophoresis or isoelectric focussing tests that detect glycosylation variants of hCG, and/or antibodies to hyperglycosylated or carbohydrate-variant hCG.

Immunoassays include, but are not limited to, assays employing specific antibodies to hyperglycosylated gonadotropin generated by standard means, and assays employing nonspecificly defined antibodies obtained by blind injections of Down's syndrome hCG or choriocarcinoma hCG into test animals using standard methods. Any type of fusion phage, monoclonal or polyclonal antibodies can be used in immunoassays of the invention, so long as the antibodies can be used in a reproducible fashion as markers for variant Down's syndrome hyperglycosylated hCG species without recognizing normal species, or as measures of the different levels observed in normal and variant populations, and specifically include antibodies to the variant carbohydrate portion of the fragments. An antibody that recognizes nicked hyperglycosylated hCG obtained from a choriocarcinoma patient but does not detect normal hCG, denominated as B152, is employed in an immunoassay described hereafter.

In a typical immunometric assay of the invention, an antibody specific for a hyperglycosylated variant such as B152 is employed as capture antibody with a second labelled antibody to hCG, β-core fragment, α-subunit, and/ or β-subunit to provide the assay with its polypeptide specificity. The label on the second antibody comprise any chemical, radioactive, lanthanide, colored dye, or genetic tag used in enzyme-linked immunosorbent assays (ELISAs), Western blots, and other sensitive and specific immunoassays and immunoradiometric assays using known methodology. These include conjugating the antibody with horseradish peroxidase or alkaline phosphatase that are easily measurable, typically using colorimetric, fluorometric or luminescent substrates. Genetic labels include firefly luciferase, employed because luciferase produces a bioluminescent molecule when incubated with its substrate, luciferin. Alternate embodiments employ a third antibody to detect the presence of the other antibodies.

Other embodiments employ the peptide-specific antibody as a capture antibody, and antibody specific to hyperglycosylated or carbohydrate-variant gonadotropin and/or an abnormal carbohydrate portion thereof comprises the second labelled antibody in any of the immunoassays described above. Competitive immunoassays employing antibodies such as B152 may also be employed to competitively detect hyperglycosylated gonadotropin. Alternate embodiments using concanavalin A or other carbohydrate-specific lectin can be used in place of the capture antibody or labelled antibody. Some embodiments employ a lectin or chromatographic method to extract carbohydrate-variant hCG prior to an immunoassay.

Carbohydrate analyses include qualitative observations of differences in physical properties between normal and Down's syndrome hCG populations described in the Examples hereafter, carbohydrate identification using plant lectins specific to the variant carbohydrate portion of Down's syndrome hCG obtained by standard lectin screening methods, or any other fingerprinting technique including qualitative or quantitative carbohydrate composition analyses. An example employing concanavalin A attached to a solid support, which binds the three mannose unit in the carbohydrate portion of hCG (FIG. 2), is employed in an embodiment illustrated hereafter, but any lectin that exhibits differential binding of hyperglycosylated versus normal hCG species can be employed in methods encompassed by the invention.

In one embodiment, for example, the presence or absence of Down's syndrome in the fetus of a pregnant woman is determined in a method which comprises obtaining a urine, saliva, plasma or serum test, sample, preferably serum or urine, from the woman, determining the carbohydrate content of the hCG in the test sample, comparing the carbohydrate content so obtained to the carbohydrate content of a corresponding control sample containing a normal hCG population, and determining the presence of Down's syndrome by observation that the carbohydrate content of the hCG population differs from the control sample. An observed increase of at least about 25%, preferably at least about 50%, in the level of at least one hyperglycosylated species is preferred. The observation of aberrant species not observed at all in normal hCG samples such as those set out in FIG. 3 is particularly preferred.

In one embodiment of the method, the presence of Down's syndrome is determined by observation that the monosaccharide content in the test sample is elevated in comparison to the control sample. This can involve an observation of differences in elution patterns such as that described below, or an analysis for N-acetylglucosamine. An increase of at least about 50% is observed in typical analyses.

Alternatively, the properties of the chorionic gonadotropin population in a sample are determined using electrophoresis, isoelectric focussing tests that detect glycosylation variants of hCG, chromatography, and mixtures of these techniques. Chromatographic methods encompass those using hydrophobic interactions or other ligand chromatography, such as that employing Blue Dextran Sepharose® (an agarose hydrophobic chromaography gel that adsorbs different proteins according to their affinity for blue dextran) illustrated hereafter, but any method of comparing physical properties of the glycopolypeptides or glycopeptides can be employed, e.g., simple qualitative observation of differences in elution patterns. These include, but are not limited to, column chromatography, coated beads, coated test tubes or plates, differential binding, extractions, and the like, and combinations of these techniques. It is an advantage of the invention that where β-core fragments are assayed, the markers are small and soluble.

Normal chorionic gonadotropin populations used as controls in many screening methods of the invention can be obtained or cloned from women containing normal karotype fetuses, or obtained commercially. hCG β-core fragments, for example, can be extracted from hCG preparations obtained from Organon, Diosynth Division (Oss, Holland) as described by Birken, et al., cited above.

Screening methods of the invention can be used alone, or in combination with other screening methods. Other screening methods include, but are not limited to, unconjugated and/or conjugated estriol measurements, hCG assays, β-core fragment analyses, free β-subunit or free α-subunit analyses, PAPP-A or CA125 analyses, α-fetoprotein analyses, inhibin assays, observations of fetal cells in serum, and ultrasound. It is an advantage of the invention that the method can replace the hCG determinations currently employed in the triple marker test described above, thereby improving its sensitivity and reliability. As mentioned previously, employing a method of the invention as a substitute for the conventional hCG assays in the triple marker or other test provides the added advantage of an early assay for Down syndrome because the hyperglycosylated hCG screens can be used in the first trimester of pregnancy. With an early diagnosis, the woman has the option of terminating her pregnancy early by non-surgical methods, with minimal mortality or fertility loss.

EXAMPLES

The following are presented to further illustrate and explain the present invention and should not be taken as limiting in any regard.

Example 1

Structural handles were sought to differentiate between Down syndrome and normal pregnancy β-core fragment. Samples of β-core fragment were purified from the urine of 6 women, 3 having normal karyotype and 3 Down syndrome second trimester pregnancies, as well as two samples from 2 diabetic patients with normal karyotype. β-Core fragments were extracted with 2 volumes of acetone at 4° C. The acetone precipitates were collected, dried, and taken up in phosphate-buffered saline (PBS). The samples were applied to a column of Blue Dextran-Sepharose™ (Pharmacia) washed with PBS, and then eluted consecutively with PBS containing 0.6 M NaCl and then PBS containing 1.0 M NaCl. β-Core fragment levels was measured in the eluates. The 3 Down's syndrome β-core fragment samples all eluted from the Blue Dextran column with the PBS containing 0.6 M NaCl, while the 5 normal karyotype samples eluted from the same columns in the next step, with PBS containing 1.0 M NaCl. This shows a difference in the physical properties of Down syndrome β-core fragment.

Figure 1:
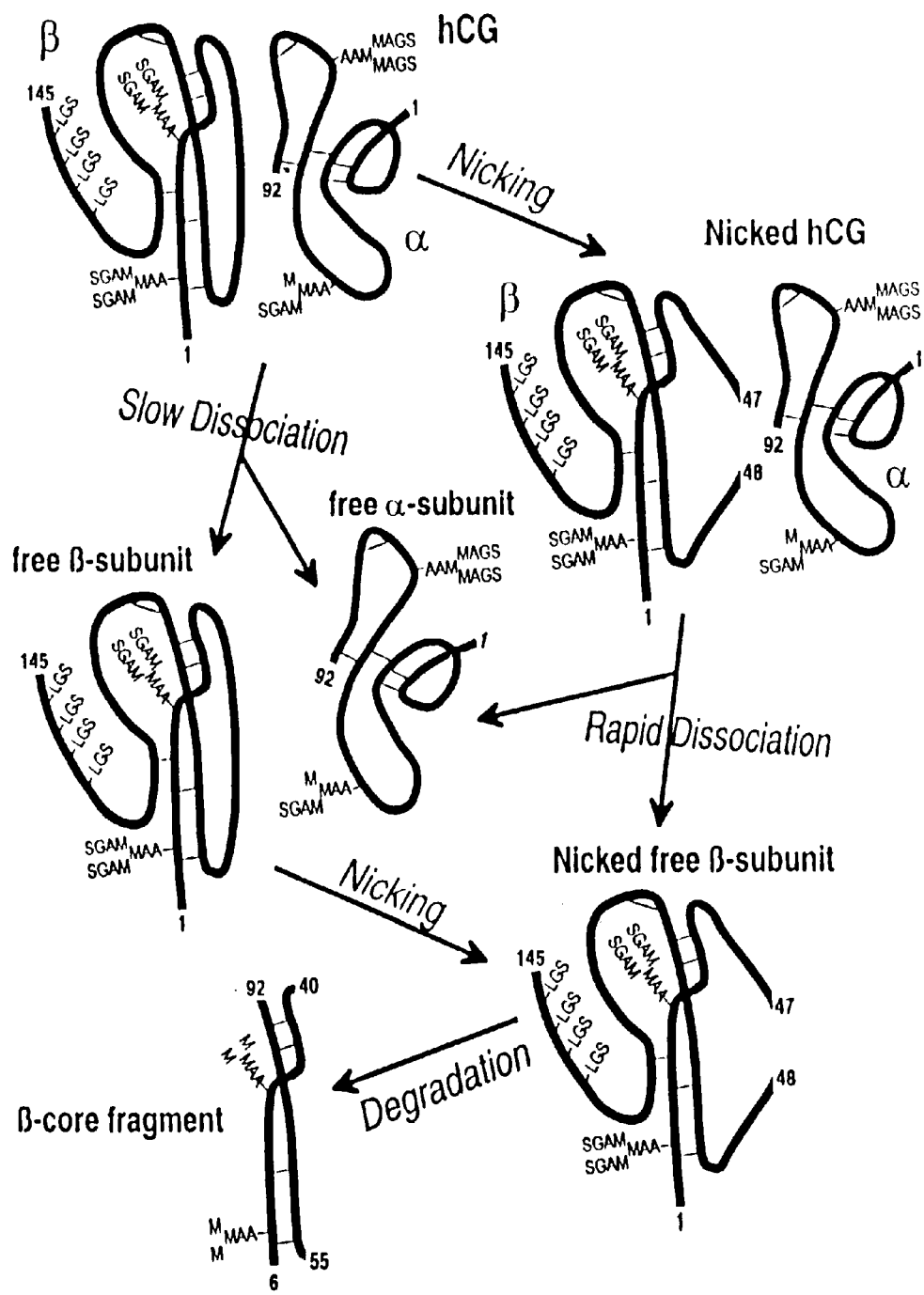
FIG. 1 is a schematic line drawing illustrating the structures of hCG related molecules. Thick lines represent the peptide backbone, numbers indicate amino acid positions, and thin lines indicate sites of disulfide linkages. The letters indicate monosaccharides in oligosaccharide side chains. S=sialic acid; G=galactose; A=N-acetylglucosamine; M=mannose; and L=N-acetylgalactosamine.

N-terminal peptide sequence analysis was conducted on the purified fragments obtained from 2 of the individual Down's syndrome β-core fragment samples, 1 individual control β-core fragment sample, and 1 β-core fragment sample purified from a pool of control urine. The purified samples all yielded an N-terminal peptide sequence identical to that described by Birken, et al., cited above. The individual and pooled control samples had a carbohydrate composition (3 mannose, 0.5 fucose, and 2 N-acetylglucosamine residues) identical to those described by Blithe, et al,. cited above, for other normal karyotype β-core fragment samples. (See structure FIG. 2B. N-Acetyl glucosamine content was determined as the hydrolysis product, glucosamine.) The 2 Down's syndrome samples, however, exhibited somewhat different compositions, with notably more N-acetylglucosamine residues (3 mannose, 1 fucose and 3.5 N-acetylglucosamine residues, and 3 mannose, 1 fucose, and 3.2 N-acetylglucosamine residues, respectively; see structure FIG. 3B). As shown in FIG. 1, β-core fragments are derived from the β-subunit of hCG. If the carbohydrate moieties on the variant Down's syndrome β-core fragment contain additional N-acetylglucosamine residues, it would be expected that β-subunit of hCG from which β-core fragment is derived would also contain different amounts of N-acetylglucosamine and likely increased amounts of sialyllactosamine antennae, depending on the mode of degradation of the subunit. The aberrant carbohydrate composition of Down's syndrome β-core fragment explains the aberrant elution profile from Blue Dextran Sepharose™.

Example 2

The binding of urine β-subunit to agarose-bound concanavalin A (Con A) was examined. Con A binds oligosaccharides and glycoproteins with biantennary-type N-linked oligosaccharides like found on normal pregnancy hCG. Glycoproteins may be released from Con A with a competitive inhibitor, α-methylmannoside. Molecules with triantennary oligosaccharides, e.g., hyperglycosylated hCG, poorly bind Con A. Hence, Con A binding was employed to screen for Down's syndrome pregnancies.

Con A-agarose, 0.15 ml, was placed in 1.5 ml conical centrifuge tubes, 0.5 ml of urine was added plus 0.5 ml PBS, pH 7.3 buffer. Tubes were rocked for 15 minutes, and then spun at 500×g to settle the gel. The unbound urine-PBS was then removed. Gels were then washed with 1 ml PBS. The wash released loosely bound proteins. The tubes were again rocked and spun, and the wash was removed. Con A was then specifically eluted with 1 ml PBS containing 0.05 M α-methylmannoside. Again tubes were rocked and spun, and the eluate was removed. The wash and eluate were then tested for free β-subunit using an immunoassay.

While the bulk of urine free β-subunit was bound and only elutable with α-methylmannoside small but varying component was loosely bound and extracted in the PBS wash. Free β-subunit (>0.5 ng/ml) was detected in 18 of 109 (17%) control samples and 9 of 15 (60%) Down syndrome sample washes. Higher levels of free β-subunit (>1.7 ng/ml) were found in 9 out of 109 (8%) control sample and 7 of 15 (47%) Down syndrome sample washes. Medians were determined for control samples at different gestation ages. Since all medians were 0 (<0.5 ng/ml), no relationship was apparent between the level of free β-subunit and gestational age. ROC analysis was used to assess the effectiveness of measurements independent of arbitrary cut-off levels. The area under the ROC curve was 0.68, indicating 68% discrimination between samples. The relationship between free β-subunit levels in the washes and in the original urine samples were determined. No correlation was observed ($r^2 < 0.5$), indicating that they are independent variables. Results indicate a higher proportion of non-Con A binding molecules, or oligosaccharide variant molecules in Down syndrome pregnancies.

β-core fragment has degraded N-linked oligosaccharides containing 2.0 N-acetylglucosamine and 0.5 fucose residues for 3.0 mannose residues (Blithe, D. L., et al., *Endocrinology* 125: 2267–2272 (1989) and Endo, T., et al., *Endocrinology* 130: 2052–2058 (1992)). Using a combination of acetone and ethanol extraction, and gel filtration, blue-Sepharose™ (a chromatography gel like Blue Dextran Sepharose® made by another company) and DEAE-Sepharose™ (a diethylaminoethl agarose chormatography gel) chromatography, β-core fragment was purified from 2 second trimester Down syndrome urines and from 2 control preparations. N-terminal peptide sequence analysis (15 rounds) was performed. The control samples contained 2.1 and 2.0 N-acetylglucosamine, and 0.6 and 0.5 fucose residues for 3.0 mannose residues, consistent with compositions indicated by Blithe, et al., and Endo, et al., cited above. The Down syndrome samples had different compositions, 3.5 and 3.2 N-acetylglucosamine, and 0.8 and 1.4 fucose residues for 3.0 mannose residues. This suggested more complex oligosaccharide structures on β-core fragment from Down syndrome.

Example 3

This example illustrates an immunoassay for Down syndrome pregnancies.

hCG preparations from individual normal pregnancy (6 women), hydatidi-form mole (3 women), and choriocarcinoma (4 women) were isolated and purified from the urine of pregnant women as previously described (Kardana, A., et al. *Endocrinology* 129: 1541–1550 (1991)). Briefly, hCG was extracted from the urines by acetone and then ethanol precipitations, followed by size-exclusion chromatography with Sephacry™ S-200 (a chromatography gel disigned for the separation of protein according to molecular size), ion exchange chromatography using DEAE-Sepharose™ and, again, by size-exclusion chromatography with high resolution Sephacryl™ S-200. During chromatography procedures, attention was given to recovering all hCG fractions.

The peptide sequence and N- and O-linked oligosaccharide structures of the various hCG forms were determined as described previously (Elliott, M., et al., *Endocrine J.*, vol. 7, 1997; see also Cole, L. A., and Birken, S., *Mol. Endocrinol.* 2: 825–830 (1988)). Monoclonal antibodies to non-nicked hCG, intact hCG, free β-subunit, β-core fragment, and choriocarcinoma hCG with hyperglycosylated N- and O-linked oligosaccharide (hCG batch C5) were prepared using the above hCG preparations following standard procedures (Ausubel, F. M., et al., *Short Protocols in Molecular Biology*, 2 nd ed., 1992, unit 11). Briefly, mice were immunized with an hCG sample, given a second imununization in about three weeks, and their spleens harvested after their blood antibody levels showed an adequate response to the sample. The cells were fused with myeloma cells, and hybridoma cells lines were obtained. Use of these monoclonals for the analysis of pregnancy urine was reported at the Third World Conference on Early Pregnancy, Oct. 3–6 1996, in abstract number 66.

The monoclonals were employed to screen urine samples analyzed using the Con A lectin procedure of Example 2. One monoclonal raised against hyperglycosylated hCG molecules (hCG batch C5) was denominated B152. It recognized <1% of normal hCG but recognized the same 60% of the samples identified as positive in the lectin assay.

The B152 monoclonal was then used to screen 139 urine samples obtained from 130 pregnant women carrying normal fetuses and 9 women carrying Down's syndrome fetuses. Hyperglycosylated gonadotropin levels were determined in a two-step sandwich immunoassay using B152 as capture antibody, and peroxidaselabelled monoclonal antibody to hCGβ, batch 4001 (Genzyme, San Carlos, Calif.) as tracer using the immunoassay methods previously described (Elliott, et al., cited above, see also Cole, L., et al., *J. Clin. Endocrinol. Metab.* 76: 704–710 (1993)). Pure hyperglycosylated gonadotropin (batch C7 described in the Cole, et al., 1988 paper cited above) was used to standardize the assay. Regular hCG (all forms of hCG dimer) levels were determined in a two-step sandwich assay using NIH CR127 hCG as a standard. Regular hCG and hyperglycosylated gonadotropin levels values are normalized to creatinine concentration as described in Example 1.

Figure 4:
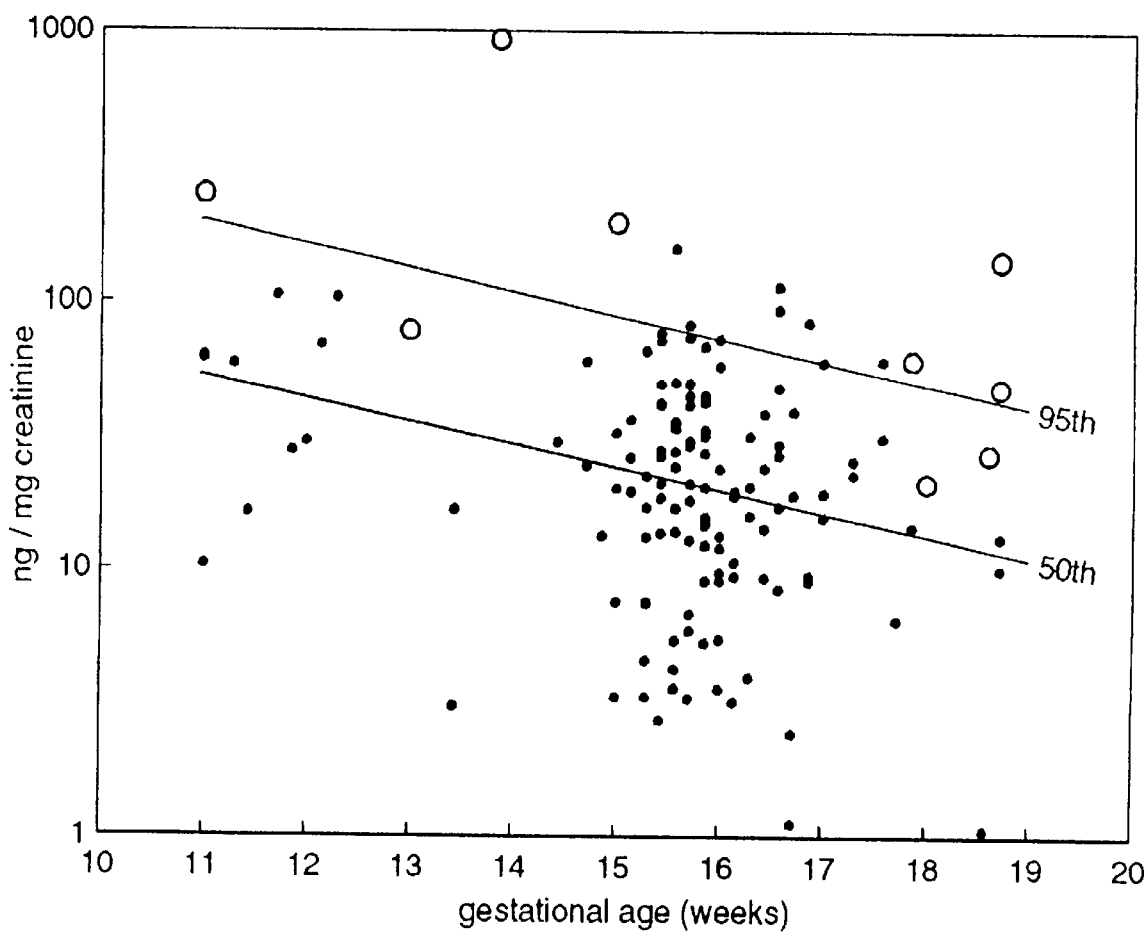
FIG. 4 is a plot of monoclonal B152 reactivity in an immunoassay for hyperglycosylated hCG in urine samples taken at the periodic intervals indicated from 130 women pregnant with normal fetuses (●) and 9 women pregnant with Down syndrome fetuses (○). Medians were determined, and samples, expressed as multiples of the normal pregnancy medians. A log Gaussian line was fitted for the normal pregnancy medians adjusted for gestational age (50th centile). The 95th centile was also determined.

Data from samples collected between 11 to 19 weeks of pregnancy are set out in the graph in FIG. 4, wherein ● represents normal sample values, and ○ represents the Down syndrome values. Results were analyzed using standard statistical methods. The gestational age specific medians for the 130 control samples all best fit a log Gaussian distribution, between the fifth and ninety-fifth centiles, for both unaffected pregnancy and Down syndrome data (expressed as multiples of the unaffected sample median, MoM). To assess screening performance, medians and log standard deviations (estimated by the 10th to 90th centile difference of the log MoM values, divided by 2.56) were determined, and the observed detection rates recorded (i.e., proportion of Down syndrome cases with levels exceeding 95th centile of unaffected pregnancies). The formula for the median line was $y=390(0.826^x)$, where y is the median and x, the gestational age. The log median of the control samples was −0.007, and the log standard deviation was 0.45. All nine Down syndrome cases exceeded the 70th centile of unaffected pregnancies. The median hyperglycosylated gonadotropin level in Down syndrome was 4.4 multiples of the unaffected median (log median=0.065). Six of the 9 Down syndrome samples (67%), including 2 of 3 first trimester and 4 of 6 second trimester cases, exceeded the 95th centile, and 3 of 9 samples (33%) exceeded the 100th centile of unaffected pregnancies.

Regular hCG levels were determined. Hyperglycosylated gonadotropin accounted for 3.7% of the regular hCG molecules in normal pregnancy (mean 29 ng/mg and 781 ng/mg creatinine, respectively), and 11% of the regular hCG molecules in Down syndrome pregnancy samples (mean 193 ng/mg and 1690 ng/mg creatinine, respectively).

The results indicate that monoclonal B152 is probably recognizing hCG carbohydrate variants, and that it can therefore be employed in an immunoassay for hyperglycosylated hCG in a method of the invention.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

The papers and patent cited above are expressly incorporated herein in their entireties by reference.

What is claimed is:

1. A method for screening for the presence or absence of Down's syndrome in the fetus of a pregnant woman which comprises obtaining a biological test sample from the pregnant woman, contacting the sample with a reagent that detects hyperglycosylated gonadotropin, removing excess reagent, and determining the presence of Down's syndrome by observation of hyperglycosylated gonadotropin in the sample not observed in corresponding samples obtained from women carrying normal fetuses.

2. A method according to claim 1 wherein the test sample is selected from the group consisting of urine, plasma and serum.

3. A method according to claim 1 wherein the sample is obtained during the first or second trimester of pregnancy.

4. A method according to claim 1 wherein observation of hyperglycosylated gonadotropin is determined using an antibody to at least one species of a chorionic gonadotropin population having aberrant carbohydrate moieties observed in Down's syndrome.

5. A method according to claim 4 wherein a lectin specific to the carbohydrate portion of hyperglycosylated gonadotropin is employed to separate species of chorionic gonadotropin having aberrant carbohydrate moieties prior to immunoassay.

6. A method according to claim 1 wherein observation of hyperglycosylated gonadotropin is determined using a lectin specific to the carbohydrate portion of Down's syndrome chorionic gonadotropin.

7. A method according to claim 1 wherein observation of hyperglycosylated gonadotropin comprises an assay for monosaccharides in the sample.

8. A method according to claim 6, wherein the lectin comprises concanavalin A.

9. A method according to claim 1, which comprises a comparison of the physical properties of the hypenglycosyated gonadotropin population in the test sample with a corresponding sample containing a normal chorionic gonadotropin population.

10. A method according to claim 9 wherein the comparison is made using a method selected from the group consisting of chromatography, electrophoresis, isoelectric focussing, and combinations of these techniques.

11. A method for screening for the presence or absence of Down's syndrome in the fetus of a pregnant woman which comprises:

(a) obtaining a biological test sample from the pregnant woman, wherein the sample is selected from the group consisting of saliva, urine, plasma, and serum;

(b) assaying for hyperglycosylated gonadotropin in the test sample using an assay selected from the group consisting of carbohydrate analysis, immunoassay using specific antibodies to hyperglycosylated gonadotropin molecules, and a combination of carbohydrate analysis and immunoassay, and (c) determining the presence of Down's syndrome by observation of hyperglycosylated gonadotropin in the sample not observed in corresponding samples obtained from women carrying normal fetuses.

12. A method according to claim 11 wherein said sample is urine or serum and the hyperglycosylated gonadotropin comprises hyperglycosylated hCG and β-core fragment.

13. A method according to claim 11 wherein the sample is obtained during the first trimester.

14. A method according to claim 11 wherein the sample is obtained during the second trimester.

15. A method according to claim 11 which employs an antibody to at least one species of a population having aberrant carbohydrate moieties observed in Down's syndrome.

16. A method according to claim 15 wherein said assaying step comprises an ELISA.

17. A method according to claim 11 wherein the assay employs a lectin specific to a variant carbohydrate portion of Down's syndrome gonadotropin.

18. A method according to claim 11, wherein the carbohydrate analysis is selected from the group consisting of chromatography, electrophoresis, isoelectric focussing, and combinations thereof.

19. A method to according to claim 2 wherein the test sample is urine.

20. A method according to claim 11 wherein the test sample is urine.

* * * * *

UNITED STATES PATENT AND TRADEMARK OFFICE
CERTIFICATE OF CORRECTION

PATENT NO.     : 6,429,018 B1  Page 1 of 1
DATED          : August 6, 2002
INVENTOR(S)    : Laurence A. Cole et al.

It is certified that error appears in the above-identified patent and that said Letters Patent is hereby corrected as shown below:

<u>Column 1,</u>
Line 9, please insert the following:
-- STATEMENT REGARDING FEDERALLY SPONSORED RESEARCH The invention was made with partial government support under NIH Grant CA46828. The government has certain rights in the invention. --

Signed and Sealed this

Twenty-third Day of November, 2004

JON W. DUDAS
*Director of the United States Patent and Trademark Office*